(12) United States Patent
Campbell et al.

(10) Patent No.: US 10,315,090 B2
(45) Date of Patent: *Jun. 11, 2019

(54) BASKETBALL TRAINING SYSTEM

(71) Applicant: Airborne Athletics, Inc., Burnsville, MN (US)

(72) Inventors: Douglas B. Campbell, Loretto, MN (US); Jeff J. Campbell, Lonsdale, MN (US); Adam T. Pan, Lonsdale, MN (US)

(73) Assignee: Airborne Athletics, Inc., Bloomington, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/803,047

(22) Filed: Nov. 3, 2017

(65) Prior Publication Data

US 2018/0050250 A1 Feb. 22, 2018

Related U.S. Application Data

(63) Continuation of application No. 14/643,889, filed on Mar. 10, 2015, now Pat. No. 9,808,696.

(51) Int. Cl.
*A63B 63/00* (2006.01)
*A63B 63/08* (2006.01)
*A63B 69/00* (2006.01)
*A63B 69/40* (2006.01)
*A63B 71/06* (2006.01)
*G06F 19/00* (2018.01)
(Continued)

(52) U.S. Cl.
CPC ........ *A63B 69/0071* (2013.01); *A63B 63/083* (2013.01); *A63B 69/408* (2013.01); *A63B 71/0616* (2013.01); *A63B 71/0622* (2013.01); *A63B 71/0669* (2013.01); *G06F 19/3481* (2013.01); *G09B 19/0038* (2013.01); *G16H 20/30* (2018.01); *A63B 2063/001* (2013.01); *A63B 2071/0683* (2013.01); *A63B 2220/17* (2013.01); *A63B 2220/58* (2013.01); *A63B 2225/093* (2013.01); *A63B 2225/20* (2013.01); *A63B 2225/305* (2013.01); *A63B 2225/50* (2013.01)

(58) Field of Classification Search
CPC .................. A63B 69/0071; A63B 69/408
USPC ....... 473/433, 432, 431, 422, 451, 436, 447; 124/6, 7, 36
See application file for complete search history.

(56) References Cited

U.S. PATENT DOCUMENTS

| 941,864 A | 11/1909 | Evans |
| 1,223,386 A | 4/1917 | Handelan |
| 2,908,266 A | 10/1959 | Cooper |

(Continued)

OTHER PUBLICATIONS

Airborne Athletics, Inc., 1 page advertising brochure, Airborne Athletics, Inc., before 2012, 1 Page.
(Continued)

*Primary Examiner* — John E Simms, Jr.
*Assistant Examiner* — Rayshun K Peng
(74) *Attorney, Agent, or Firm* — Fish & Richardson P.C.

(57) ABSTRACT

A basketball training system includes a ball delivery system in which a basketball is delivered to a ball ready holder located in front of a ball launch mechanism. A launch arm is grabbed and pulled backward against a spring force, and then is released to pivot forward and strike the basketball from the ball ready holder.

18 Claims, 16 Drawing Sheets

(51) Int. Cl.
*G09B 19/00* (2006.01)
*G16H 20/30* (2018.01)

(56) References Cited

U.S. PATENT DOCUMENTS

| | | |
|---|---|---|
| 3,776,550 A | 12/1973 | McNabb |
| 3,814,421 A | 6/1974 | Spier, Jr. |
| 3,878,828 A | 4/1975 | Francesco |
| 3,917,263 A | 11/1975 | Wiley |
| 4,168,695 A | 9/1979 | Haller et al. |
| 4,262,648 A | 4/1981 | Wegener et al. |
| 4,471,746 A | 9/1984 | Ando |
| 4,579,340 A | 4/1986 | Jenkins et al. |
| 4,667,957 A | 5/1987 | Joseph |
| 4,678,189 A | 7/1987 | Koss |
| 4,714,248 A | 12/1987 | Koss |
| 4,913,431 A | 4/1990 | Jakobs |
| 4,936,577 A | 6/1990 | Kington et al. |
| 4,940,231 A | 7/1990 | Ehler |
| 4,955,605 A | 9/1990 | Goldfarb |
| 4,995,371 A * | 2/1991 | Kuizinas ............ A63B 47/002 124/36 |
| 5,016,875 A | 5/1991 | Joseph |
| 5,035,423 A | 7/1991 | Arciniega |
| 5,125,651 A | 6/1992 | Keeling et al. |
| 5,183,253 A | 2/1993 | Grimaldi et al. |
| 5,312,099 A | 5/1994 | Oliver, Sr. |
| 5,393,049 A | 2/1995 | Nelson |
| 5,409,211 A | 4/1995 | Adamek |
| 5,417,196 A | 5/1995 | Morrison et al. |
| 5,540,428 A | 7/1996 | Joseph |
| 5,601,284 A | 2/1997 | Blackwell et al. |
| 5,676,120 A | 10/1997 | Joseph |
| 5,681,230 A * | 10/1997 | Krings ............... A63B 63/083 124/26 |
| 5,746,668 A | 5/1998 | Ochs |
| 5,771,018 A | 6/1998 | Kennedy |
| 5,776,018 A | 7/1998 | Simpson et al. |
| 5,813,926 A | 9/1998 | Vance |
| 5,842,699 A | 12/1998 | Mirando et al. |
| 5,911,214 A * | 6/1999 | Andrews ............ A63B 69/408 124/16 |
| 5,980,399 A * | 11/1999 | Campbell ........... A63B 69/409 124/61 |
| 6,224,503 B1 * | 5/2001 | Joseph ............... A63B 63/083 124/6 |
| 6,302,811 B1 | 10/2001 | Topham |
| 6,458,049 B2 | 10/2002 | Bush |
| 6,659,893 B1 | 12/2003 | Campbell et al. |
| 7,288,034 B2 | 10/2007 | Woodward et al. |
| 8,147,356 B2 | 4/2012 | Campbell et al. |
| 8,206,246 B2 | 6/2012 | Joseph et al. |
| 8,286,619 B2 | 10/2012 | Mihaljevic |
| 2009/0137347 A1 | 5/2009 | Jenkins et al. |
| 2010/0261557 A1 | 10/2010 | Joseph et al. |
| 2012/0142454 A1 | 6/2012 | Campbell et al. |
| 2013/0005512 A1 | 1/2013 | Joseph et al. |
| 2013/0157786 A1 | 6/2013 | Joseph et al. |

OTHER PUBLICATIONS

Brochure entitled "Sniper: the Ultimate basketball Trainer," before Oct. 22, 1995, 5 pages including the cover letter.
Shoot-A-Way, Brochure entitled "The All New 800 Series Gun," before Dec. 12, 2011, 12 Pages.
Brochure entitled "The Shoot Away: The Perfect Shooting Aide," before Dec. 2, 2011, 1 Page.

* cited by examiner

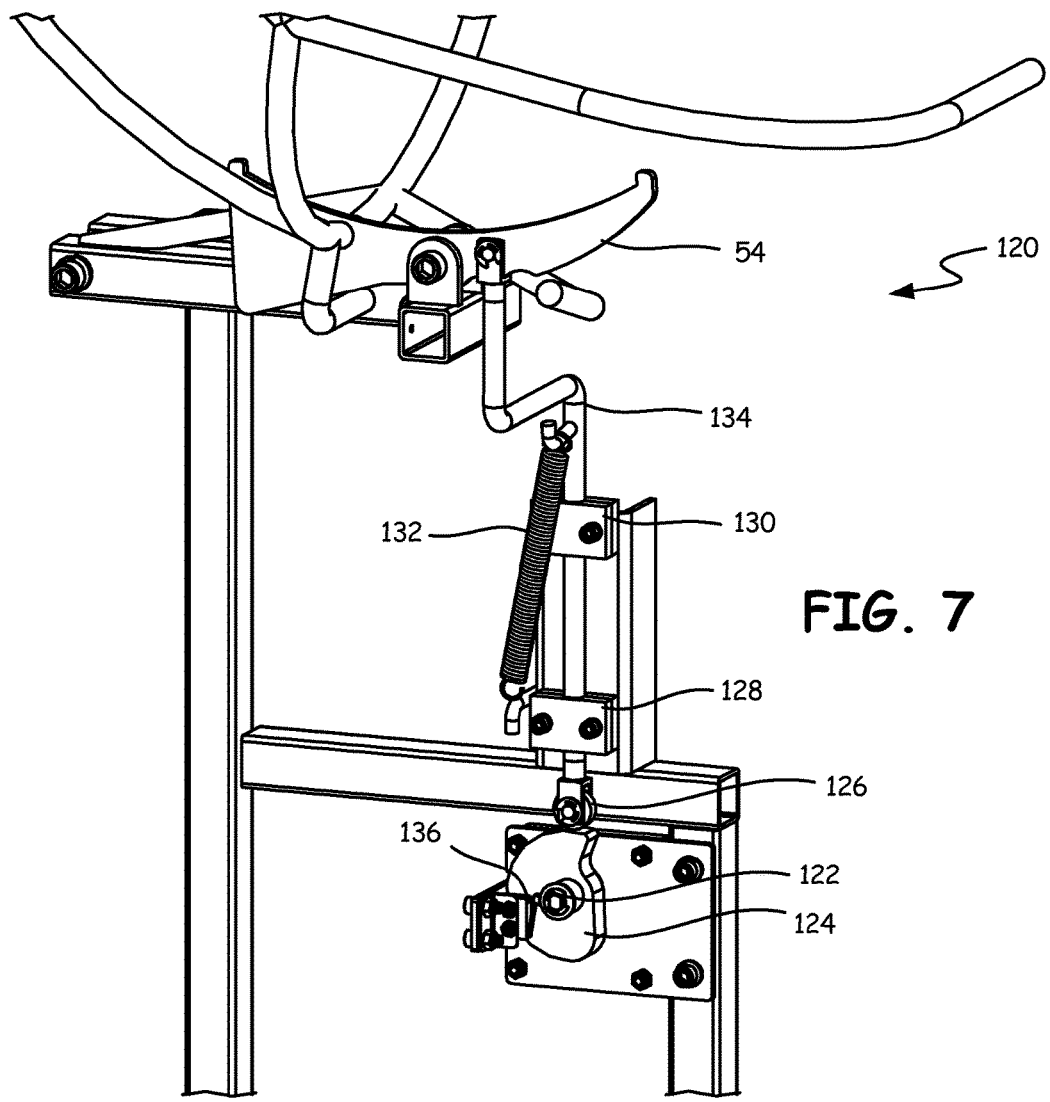

BASKETBALL TRAINING SYSTEM

CROSS-REFERENCE TO RELATED APPLICATION(S)

This application is a continuation of U.S. application Ser. No. 14/643,889 filed Mar. 10, 2015 for "BASKETBALL TRAINING SYSTEM" by D. Campbell, J. Campbell and A. Pan.

BACKGROUND

The present invention relates to sports training, and in particular to a basketball training machine with a motorized ball delivery device.

Training in sports involves the development of skills as well as physical conditioning. The game of basketball requires physical strength and conditioning, and also requires special skills. Successful development of those skills requires repetition during practice.

Although it is a team sport, basketball presents opportunities for an individual player to practice and improve his or her game without the need for other players to be present. A player can develop ball handling skills and shooting skills through individual practice.

Basketball players develop their shooting skills by shooting the basketball from various locations on the court. If a second player is not present to rebound, the shooter must rebound his or her own shots. The rebounding process can waste time that could otherwise be used in taking more shots. Over the past several decades, a number of ball collecting devices have been developed to collect basketball shot at the basketball goal (i.e. the backboard and the attached hoop and net). The ball collecting devices generally include netting and a frame for supporting the netting around the basketball goal. The ball collecting devices are often used with a ball delivery device, which directs the ball back to the player.

Motorized ball delivery devices can return basketballs to a shooter at various locations on a basketball court. The ball delivery device can have programs that determine which direction to return balls to the player, how many times to return the ball, etc.

Some basketball training systems also calculate shooting percentage. The system monitors how many balls are delivered to the player (which represents a number of shots taken), and how many shots go through the basketball hoop (i.e. shots made). The system calculates a shooting percentage based on the number of shots taken and the number of shots made.

SUMMARY

A basketball training system includes a ball delivery system in which a basketball is delivered to a ball ready holder located in front of a ball launch mechanism. A launch arm is grabbed and pulled backward against a spring force, and then is released to pivot forward and strike the ball from the ball ready holder.

BRIEF DESCRIPTION OF THE DRAWINGS

FIG. 7 is a perspective view of a toggle arm actuator mechanism of the ball delivery system.

DETAILED DESCRIPTION

Figure 1:
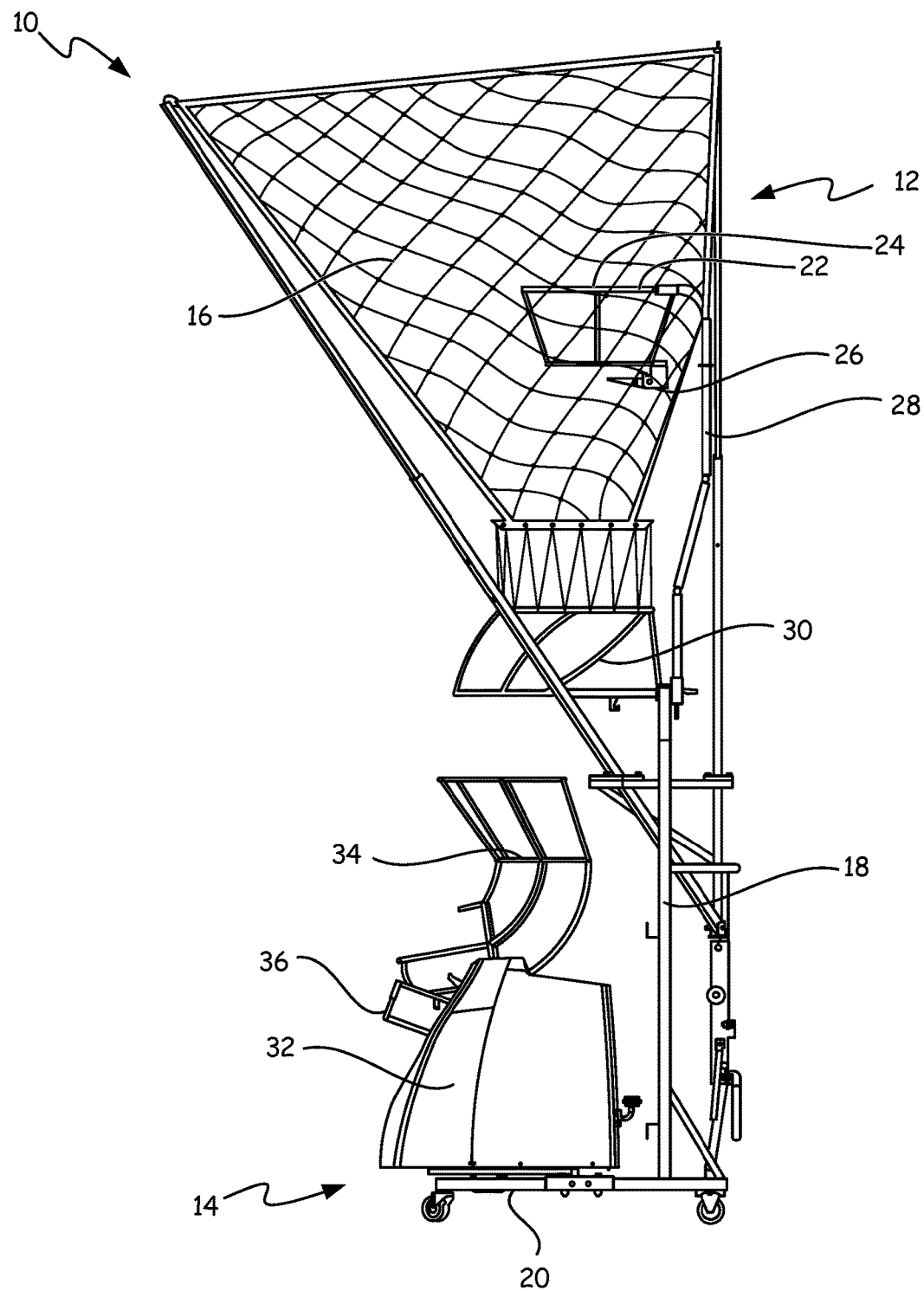
FIG. 1 is a side view of a basketball training machine that includes a ball collection system and a ball delivery system.

FIG. 1 shows a side view of basketball training machine 10. Basketball training machine 10 includes two main systems, ball collection system 12 and ball delivery system 14.

Ball collection system 12 includes net 16, net frame 18, base 20, shots made counter 22 (which includes made shots funnel 24, shots made sensor 26, and counter support frame 28), and upper ball feeder 30. When machine 10 is used for shooting practice, net 16 is positioned in front of a basketball backboard (not shown) so that the basketball hoop and net (not shown) are immediately above shots made counter 22. The size of net 16 is large enough so that missed shots (which do not go through the basketball hoop and net and through shots made counter 22) will still be collected by net 16 and funneled down to upper ball feeder 30.

Ball delivery system 14 includes ball launching machine 32, main ball feeder 34, and ball ready holder 36. Ball launching machine 32 is pivotally mounted on base 20. The inlet of main ball feeder 34 is positioned immediately below the outlet of upper ball feeder 30. Ball launching machine 32 is pivotable about an axis that is aligned with the inlet of main ball feeder 34 and the outlet of upper ball feeder 30. Balls drop out of upper ball feeder 30 into main ball feeder 34. Balls are delivered one at a time from main ball feeder 34 into ball ready holder 36 at the front of ball launching machine 32. Launch arm 38 (shown in FIG. 2) launches the basketball out of holder 36 to a location on the floor where the player catches the ball and shoots. The location on the floor where the ball is delivered can be changed by pivoting machine 32 with respect to base 20.

Figure 2:
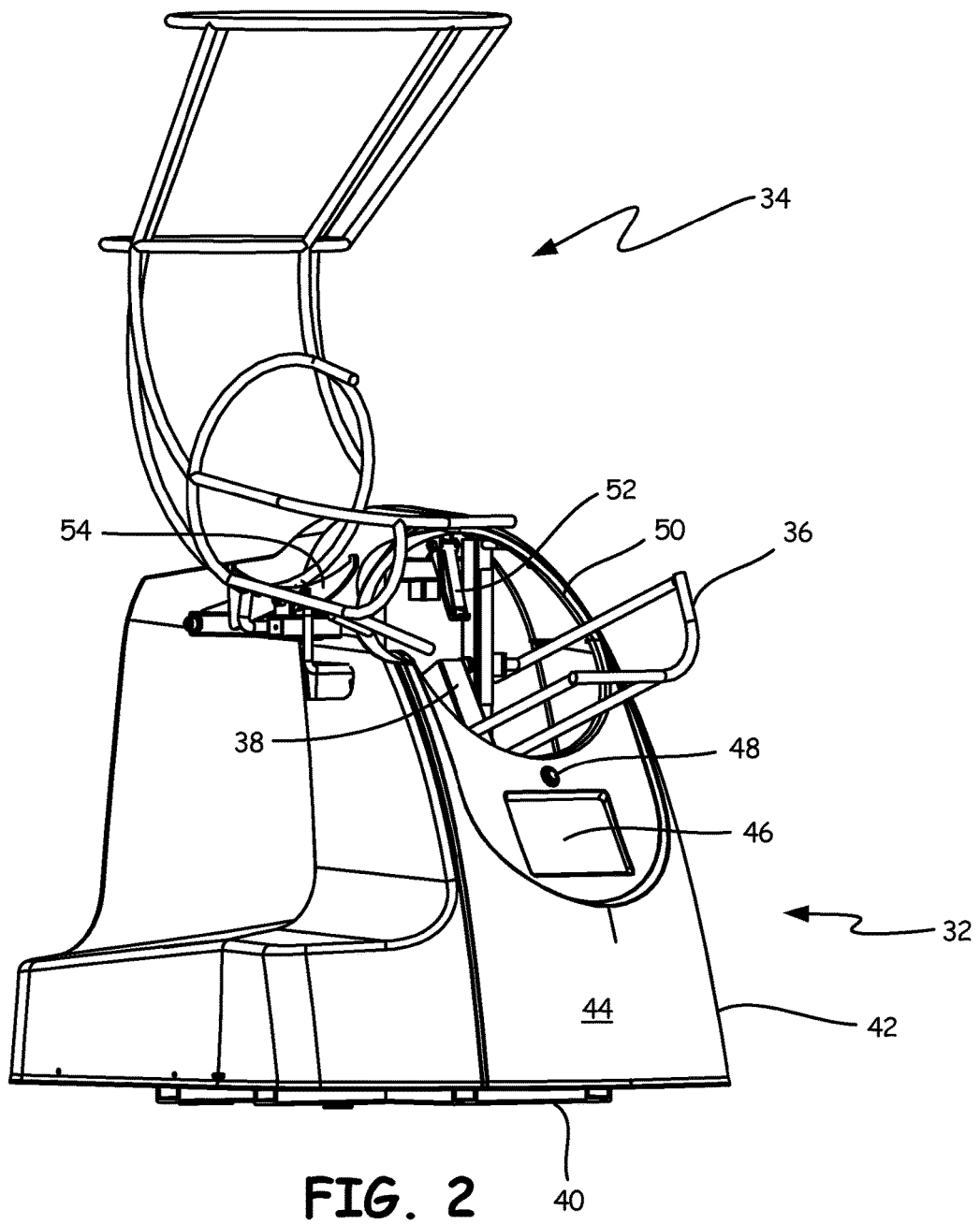
FIG. 2 is a front perspective view of the ball delivery system of FIG. 1.

FIG. 2 is a perspective view of ball delivery system 14 from the front and left of ball launching machine 32. In this view, ball collection system 12 is not shown. Ball delivery system 14 includes ball launching machine 32, to which main ball feeder 34 and ball ready holder 36 are mounted. Ball launching machine 32 includes launch arm 38, bottom platform 40 (which is pivotably mounted to base 20 of ball collection system 12), and outer shell 42 (which encloses the ball launching mechanism and controls that operate machine 32. Front face 44 of outer shell 42 includes electronic front display 46, pre-launch warning light 48 and front opening 50. Also shown in FIG. 2 are ball ready lever 52 and toggle arm 54.

Balls that are collected by ball collection system 12 enter the upper end of main ball feeder 34 and directed downward and forward to toggle arm 54, which stops further ball movement. When toggle arm 54 is actuated, it pivots to release a single ball to travel further downward and forward into ball ready holder 36. As shown in FIG. 2, ball ready holder 36 slopes downward and rearward through opening 50 into ball launching machine 32. As the ball rolls down ball ready holder 36 toward launch arm 38, it contacts ball ready lever 52. When ball ready lever 52 is depressed by a ball in ball ready holder 36, it provides a ball ready input signal to the control system of machine 32. This causes a motor driven cycle to be initiated in which launch arm is engaged and pulled backward while a tension spring is extended. As the cycle continues, launch arm 38 is released and the spring force drives launch arm 38 forward to hit the ball and launch it forward out of machine 32 and ball ready holder 36.

Figure 3:
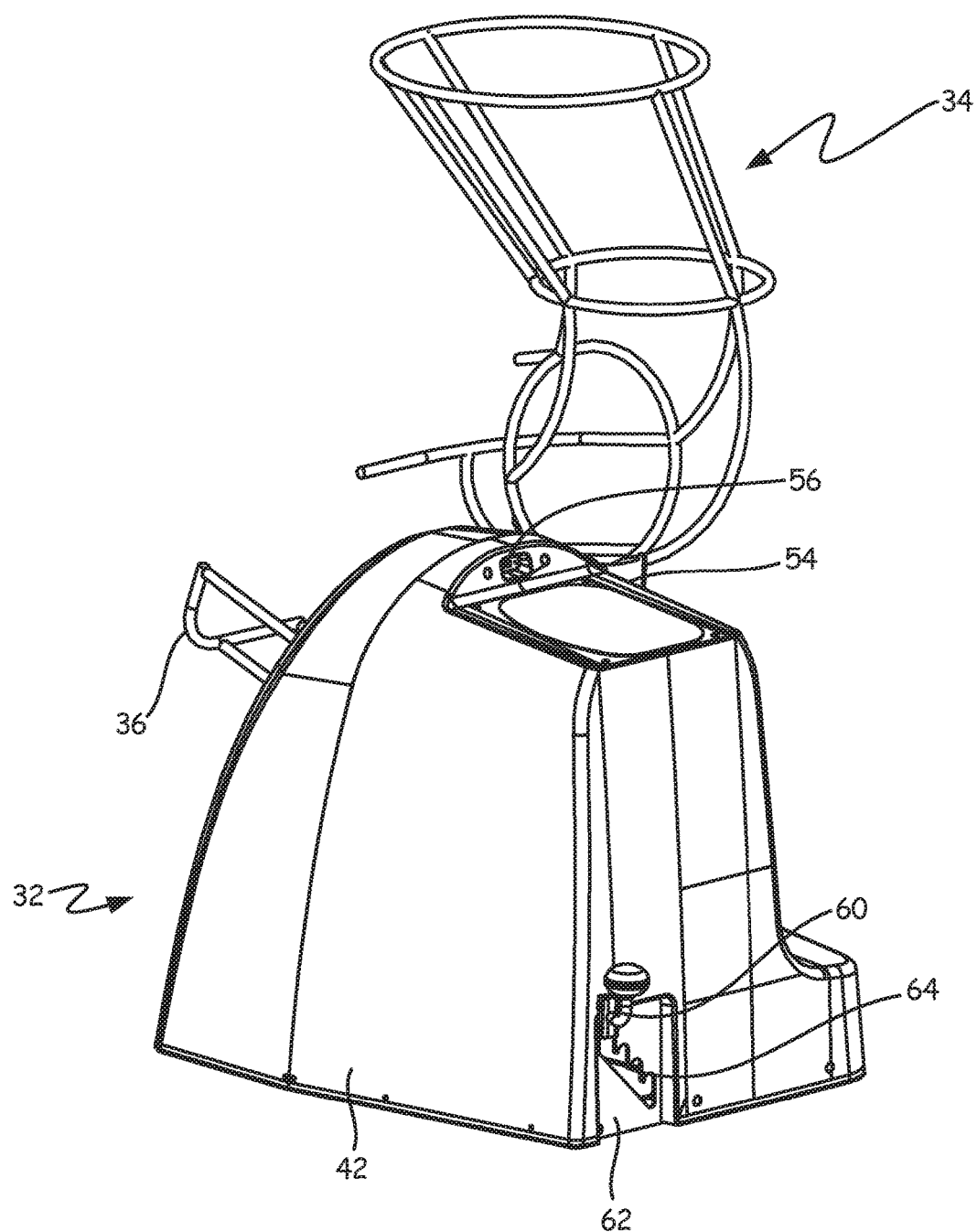
FIG. 3 is a rear perspective view of the ball delivery system of FIG. 1.

FIG. 3 is a perspective view of ball delivery system 14 from the rear and right of machine 32. At the top of shell 42 are USB port 56 and console 58, which allow a user to input information and select operating modes of machine 32, and to receive outputs including data collected by machine as well as menus, instructions, and prompts.

At the rear of machine 32 are ball distance adjustment knob 60 and ball distance pre-select plate 62. Knob 60 and plate 62 are used to change the spring tension or preload on the spring that drives launch arm 38. The greater the preload, the further the distance the ball will be driven by launch arm 38 when it is released. In the embodiment shown in FIG. 3, plate 62 contains diagonal notched track 64, which includes five notches at which the tension rod connected to adjustment knob 60 can be positioned. The lower the position of knob 60, the greater the preload and the farther the ball will be launched.

Figure 4:
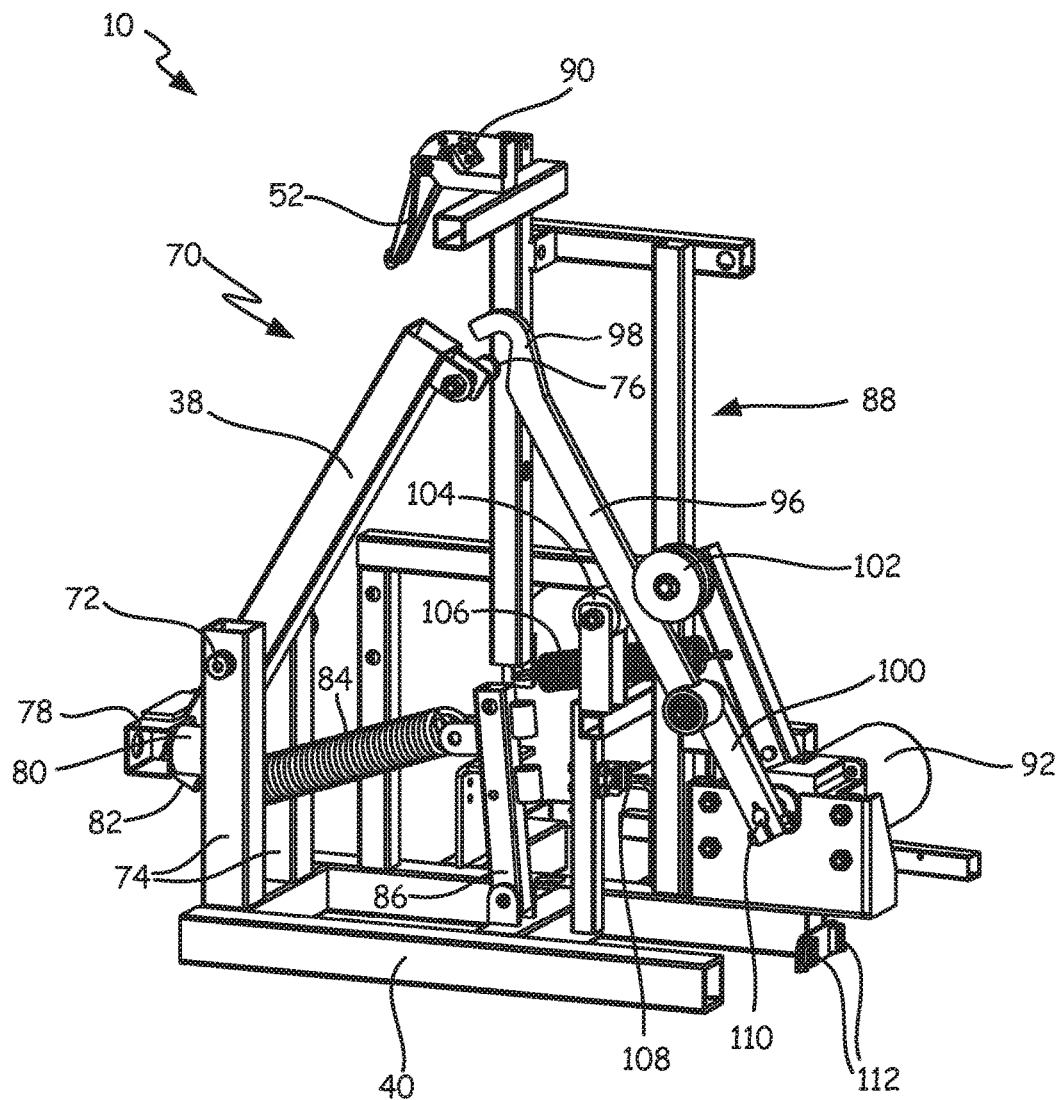
FIG. 4 is a perspective view of the ball launch mechanism of the ball delivery system.

FIG. 4 is a perspective view of ball launch mechanism 70 built on base frame 40, which is rotatably mounted to base 20 of ball collection system 12. Ball launch mechanism 70 launches balls using launch arm 38, which is pivotally mounted by pivot pin 72 to arm support uprights 74. At its upper end, launch arm 38 carries grab pin 76. At its lower end, launch arm 38 carries cross bar 78. Mounted to cross bar 78 are bumpers or cushions 80, which engage arm support uprights 74 to stop rearward movement of the lower end of launch arm 38 (and limit the forward movement of the upper end of strike are 38). Bracket 82 is mounted to the lower end of launch arm 38 and connects the forward end of throw spring 84 to the lower end of launch arm 38. The rear end of throw spring 84 is connected to the upper end of throw spring tensioner 86. As shown in FIG. 4, the lower end of throw spring tensioner 86 is pivotally connected to platform 40. The position of throw spring tensioner 86, and thus the tension or preload of throw spring 84 is controlled by a linkage between ball distance adjustment knob 60 and tensioner 86. This will be shown in FIGS. 5A and 5B.

Ball ready lever 52 is positioned above the upper end of launch arm 38 in FIG. 4. Ball ready lever 52 is mounted at the top of support framework 88, which extends upward from platform 40 and includes a number of vertical and horizontal tubular members. Ball ready sensor 90 is mounted adjacent ball ready lever 52, so that when a ball rolls backward and downward in ball ready holder 36 and presses lever 52, ball ready sensor 90 changes state to indicate that a ball is in place and is ready to be launched.

The retracting and then release of launch arm 38 is performed by a motorized drive system that includes drive motor 92, crank arm 94, grab arm 96 with hook 98, guide arm 100, movable guide wheel 102, stationary guide wheel 104, guide arm spring 106, and drive motor sensor 108. Crank arm 94 is fixedly connected at its inner end to shaft 110 of motor 92, and is pivotally connected at its outer end to the lower end of grab arm 96. As crank arm 94 is rotated through a 360 degree cycle by motor 92, grab arm 96 is guided between movable guide wheel 102 and stationary guide wheel 104. Guide arm spring 106 applies a spring bias to movable guide when 102 to keep guide wheel 102 in engagement with grab arm 96 so that grab arm 96 is contained between movable guide arm 102 and stationary guide wheel 104.

During a cycle, grab arm 96 will be moved so that hook 98 engages grab pin 76 and pulls the upper end of launch arm 38 rearward against the string force of throw spring 84. As the cycle continues, grab pin 76 will be pulled rearward to a maximum distance. Further rotation of crank arm 94 causes hook 98 to disengage from grab pin 76, which releases launch arm 38 to move forward and launch the ball sitting on ball ready holder 36. The distance that the ball will travel depends on the amount of preload applied to throw spring 84 through throw spring tensioner 86.

The cycle is limited to one rotation of motor shaft 110. Drive motor sensor 108 is engaged by crank arm 94 as the cycle is being completed, and causes the cycle to be ended.

FIG. 4 also shows rotation calibration sensors 112 that are mounted on platform 40. These sensors are used to determine the center position of platform 40, which allows machine 32 to calibrate the rotation potentiometer that keeps track of the positon on the floor where the ball is being delivered.

Figure 5A:
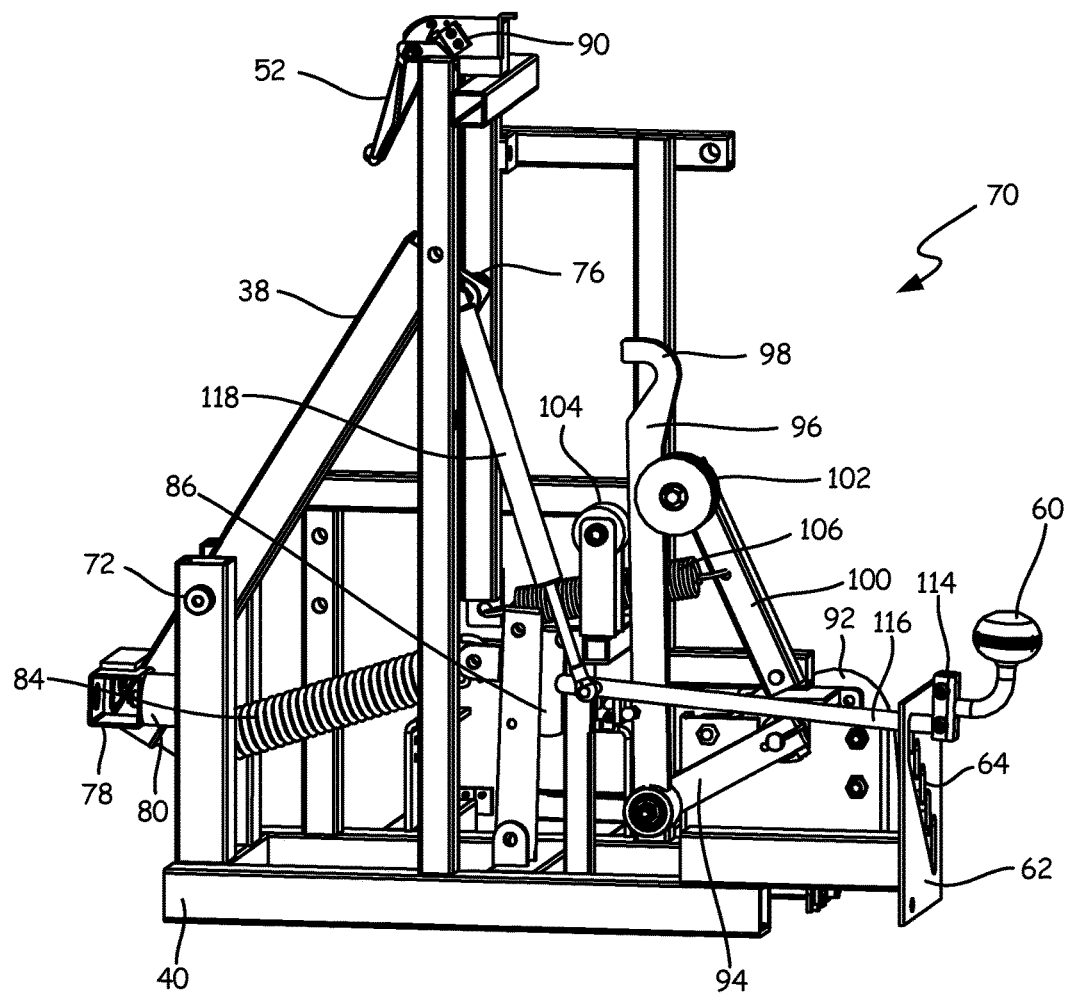
FIGS. 5A and 5B show the spring preload mechanism of the ball launch mechanism in two different positions.
Figure 5B:
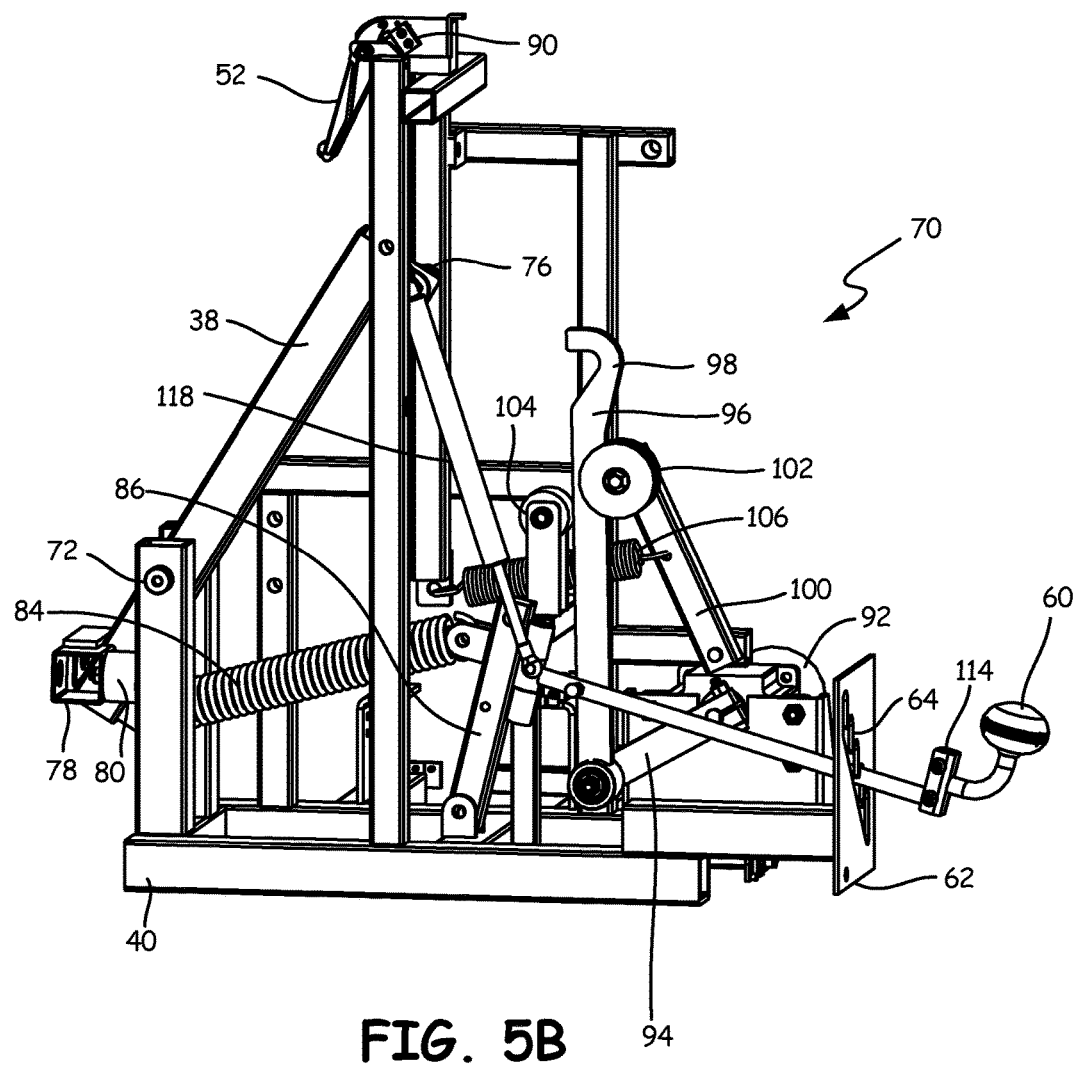

FIGS. 5A and 5B show ball launch mechanism 70 with the mechanism for preloading throw spring 84 in place. Both FIGS. 5A and 5B show launch mechanism 70 after grab arm 96 has released grab pin 76 and launch arm 38 has moved forward and launched the ball. Bumpers 80 are positioned against arm support uprights 74. As seen, grab arm 96 is oriented vertically and hook 98 is rearward of grab pin 76. Shown in FIGS. 5A and 5B are ball distance adjustment knob 60, ball distance pre-select plate 62, track 64, clamp 114, tension rod 116, and spring assist 118. Tension rod 116 is connected at its outer end to knob 60 by clamp 114, and is connected at its inner end to throw spring tensioner 86. Spring assist 118 has its lower end connected to tension rod 116 near throw spring tensioner 86, and is connected at its upper end to support framework 88. The angle of tensioner 86, and thus the amount of tension preload on throw spring 84, depends on which notch of track 64 is holding tension rod 116. FIGS. 5A and 5B illustrate two of the possible positions of tension rod 116.

FIGS. 6A-6F illustrate a cycle of the drive system that retracts and then releases launch arm 38 to launch a ball. In FIGS. 6A-6F, throw spring 84 is not shown for simplicity and clarity. The starting and ending point for each cycle is with grab arm 96 in a vertical orientation and hook 98 rearward of grab pin 76 and launch arm 38. That position is shown as the start/end position in FIG. 6A.

Figure 6A:
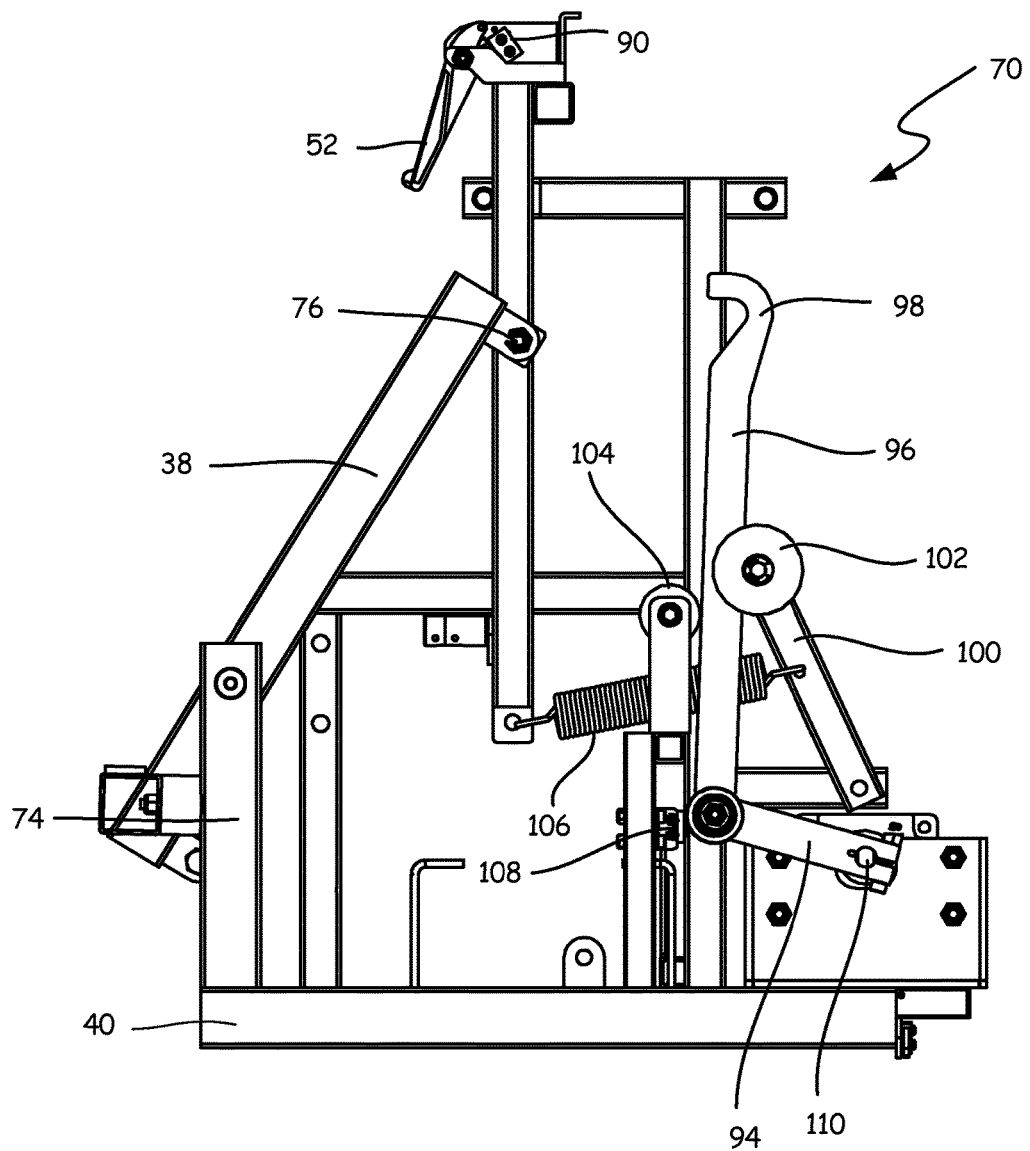
FIGS. 6A-6F illustrate one complete cycle of operation of the ball launch mechanism.

FIG. 6A shows the outer end of crank arm 94 in contact with drive motor sensor 108. Motor 92 is stopped, grab arm 94 is nearly vertical and is held between guide wheels 102 and 104. The upper end of launch arm 38 and grab pin 76 are at their forward most position. In response to a signal from ball ready sensor 90 indicating a ball is in position on ball ready holder 36 (not shown), drive motor 92 is activated and begins to rotate motor shaft 110 and crank arm 94 in a clockwise direction.

Figure 6B:
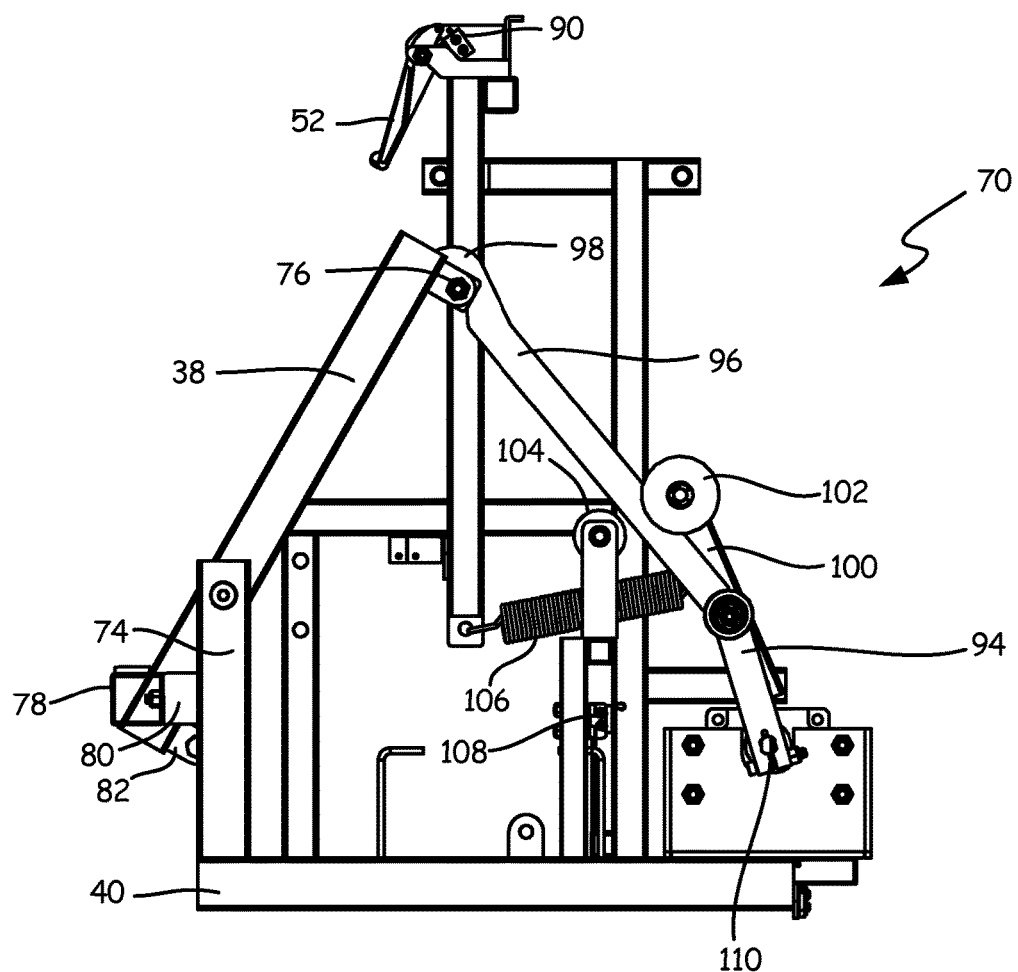

FIG. 6B shows the cycle at the point where crank arm 94 has rotated to a position where grab arm 96 is lifted away from stationary guide wheel 104. The spring bias provided by guide arm spring 106 to movable guide wheel 102 has caused grab arm 96 to pivot so that hook 98 moves forward over grab pin 76.

Figure 6C:
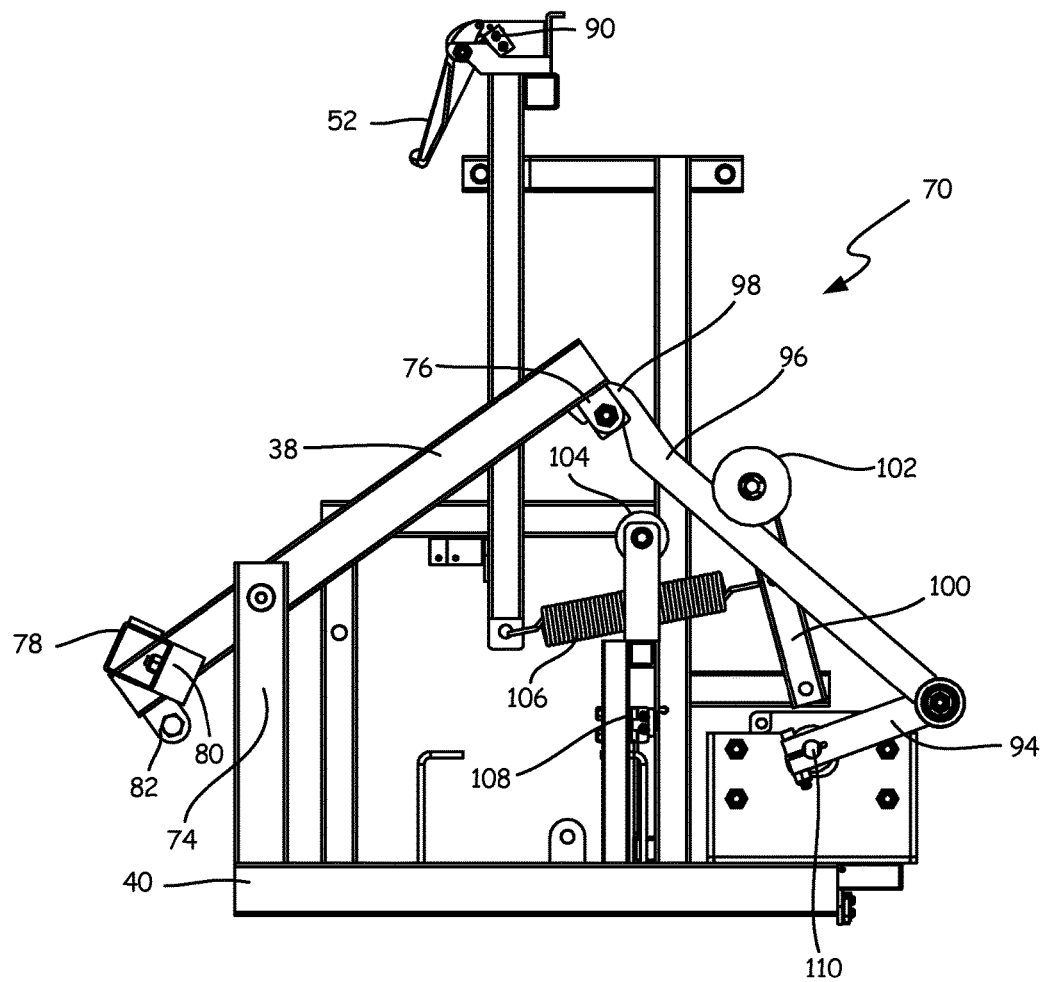

FIG. 6C shows grab arm 96 pulling grab pin 76 and launch arm 38 rearward as crank arm continues its clockwise rotation. Movable guide wheel 102 and guide arm spring 106 keep hook 98 in engagement with grab pin 76.

Figure 6D:
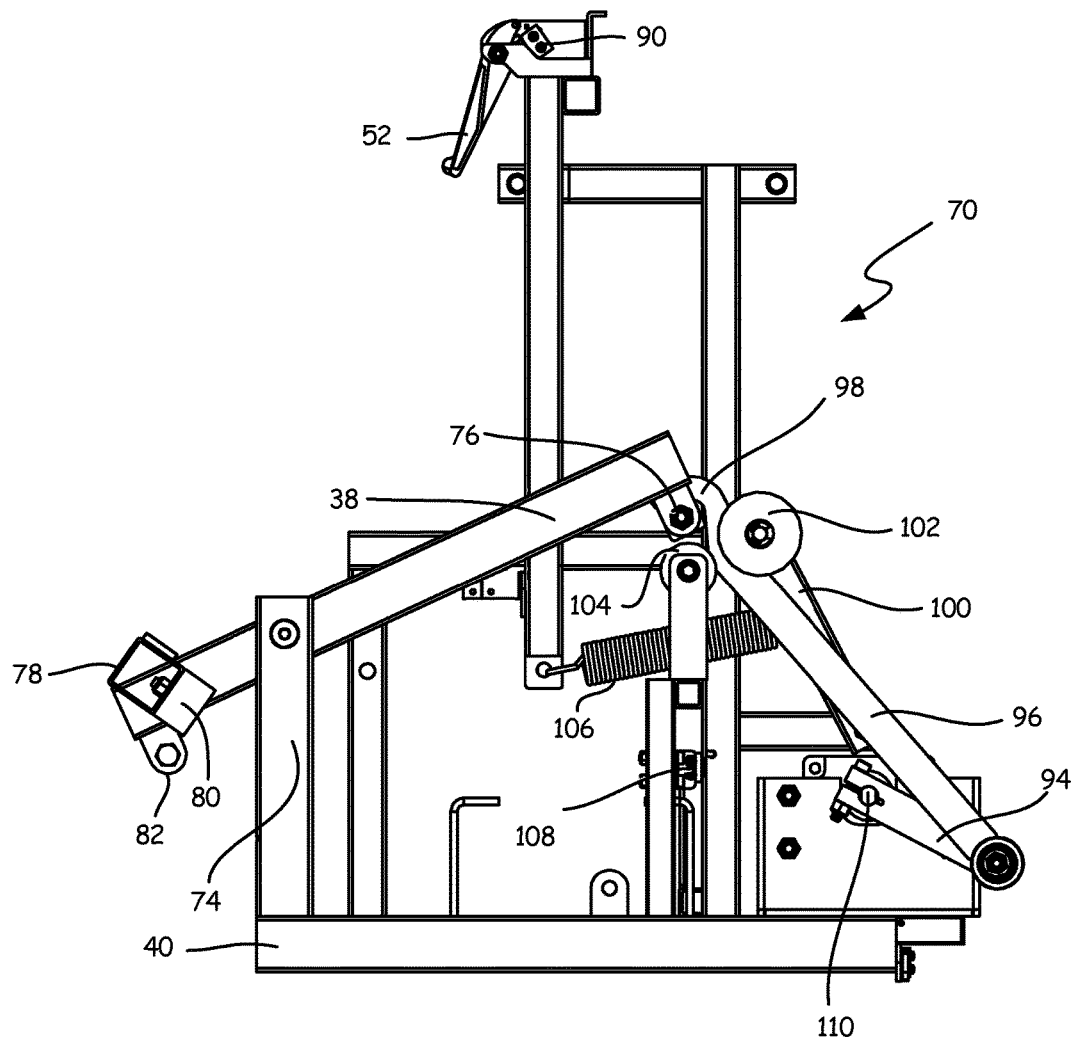
Figure 6E:
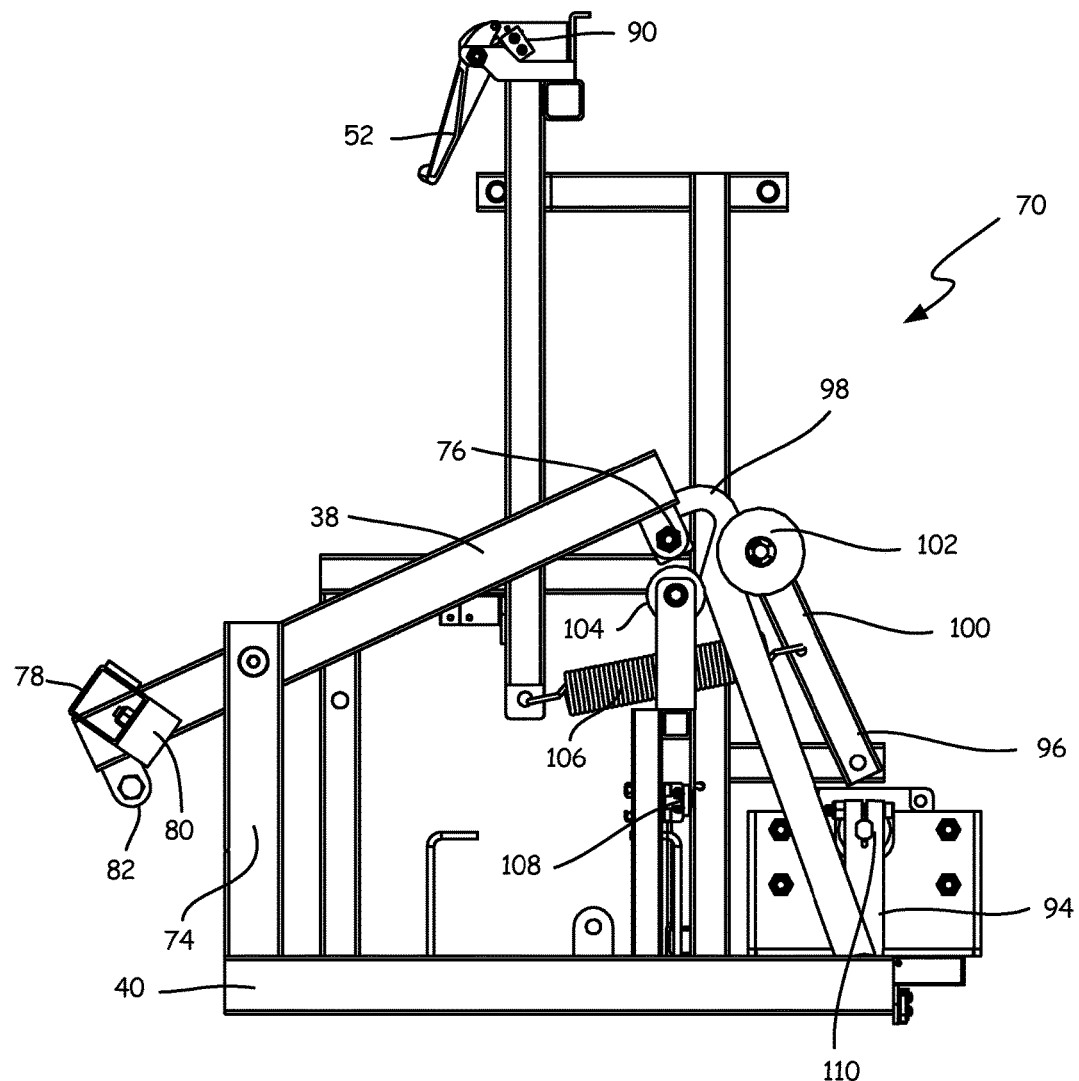

FIG. 6D show grab pin 76 at its furthest rearward and downward position. Further clockwise rotation of crank arm 94 will begin to cause hook 98 to disengage for grab pin 76, as illustrated in FIG. 6E.

Figure 6F:
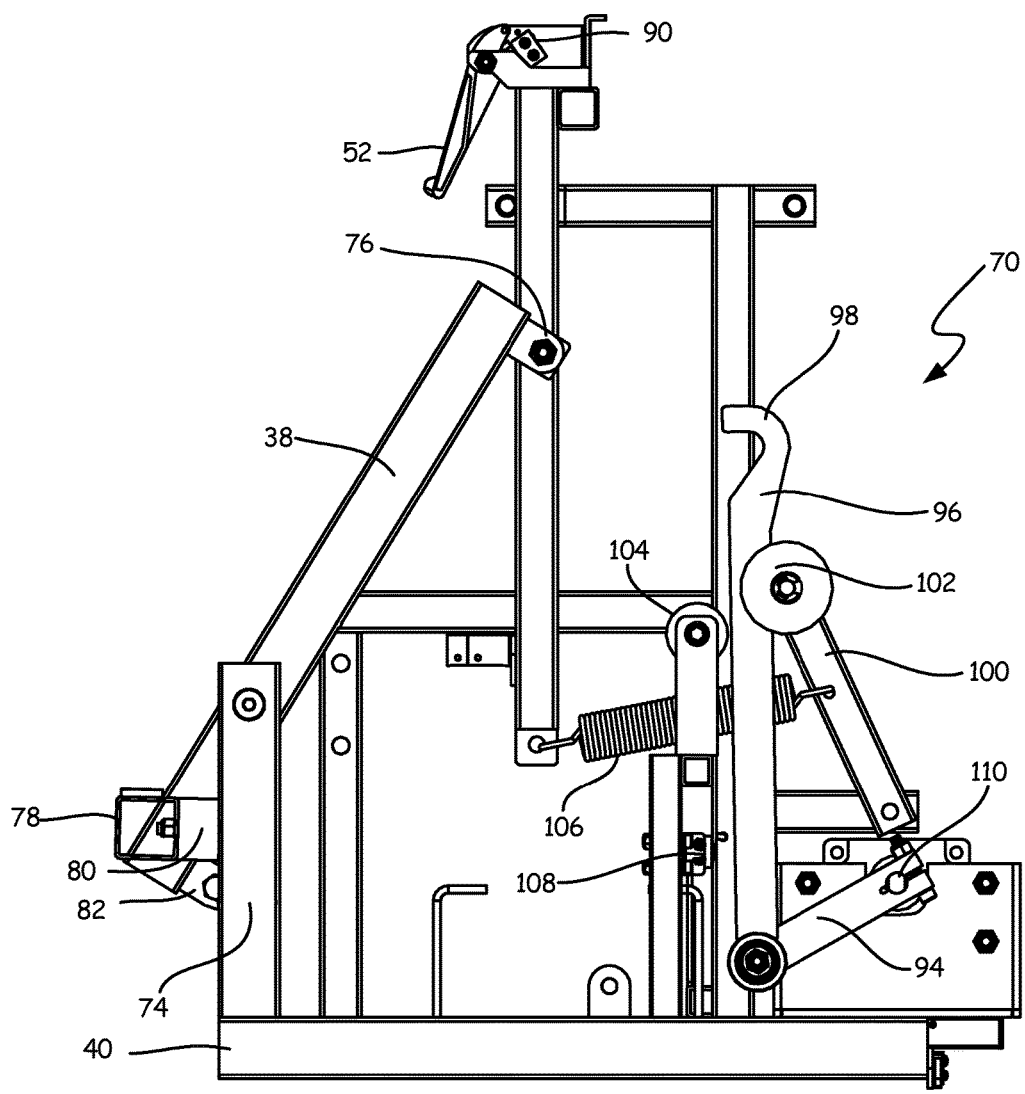

In FIG. 6F, hook 98 has released grab pin 76 and the upper end of launch arm 38 has moved forward rapidly to strike and launch the ball. At the point shown in FIG. 6F, the cycle is not yet complete. Crank arm will continue to rotate in the clockwise direction until the outer end of crank arm 94 engages drive motor sensor 108. At that point, drive motor 92 stops with the mechanism in the position shown in FIG. 6A.

FIG. 7 shows toggle arm actuator mechanism 120, which operates toggle arm 54. Mechanism 120 includes motor shaft 122, cam 124, cam follower guide wheel 126, guide blocks 128 and 130, spring 132, toggle rod 134, and sensor 136. When a ball has been launched, ball ready sensor 90 indicates that there is no longer a ball waiting in ball ready holder 36 to be launched. That initiates cam drive motor 150 (shown in FIG. 9) to rotate motor shaft 122 in a counter-clockwise direction. As motor shaft 122 rotates, cam 124 rotates and guide wheel 126 follows the contour of cam 124. Spring applies a downward spring bias to toggle rod 134 to ensure the guide wheel 126 and toggle rod 134 will follow cam 124. When guide wheel 126 and toggle rod 134 move downward, the upper end of toggle rod 134 pulls the forward end of toggle arm 54 downward to release one ball downward and forward into ball ready holder 36. As motor shaft 122 and cam 124 continue to rotate in a counterclockwise direction, guide wheel 126 and toggle rod 134 are driven upward to block any further ball from moving past toggle arm 54. The rotation of motor shaft 122 continues until sensor 136 signals that one complete revolution has been completed.

The coordinated operation of ball launch mechanism 70 and toggle arm actuator mechanism 120 causes balls collected by ball collection system 12 and delivered to main ball feeder 34 to be supplied one at a time onto ball ready holder 36. When a ball is in position on ball ready holder 36, launch mechanism 70 initiates a cycle in which grab arm 96 retracts launch arm 38 and loads throw spring 84, and then releases launch arm 38 so that the spring force causes launch arm 38 to strike the ball and launch the ball off ball ready holder 36 to the player.

Figure 8:
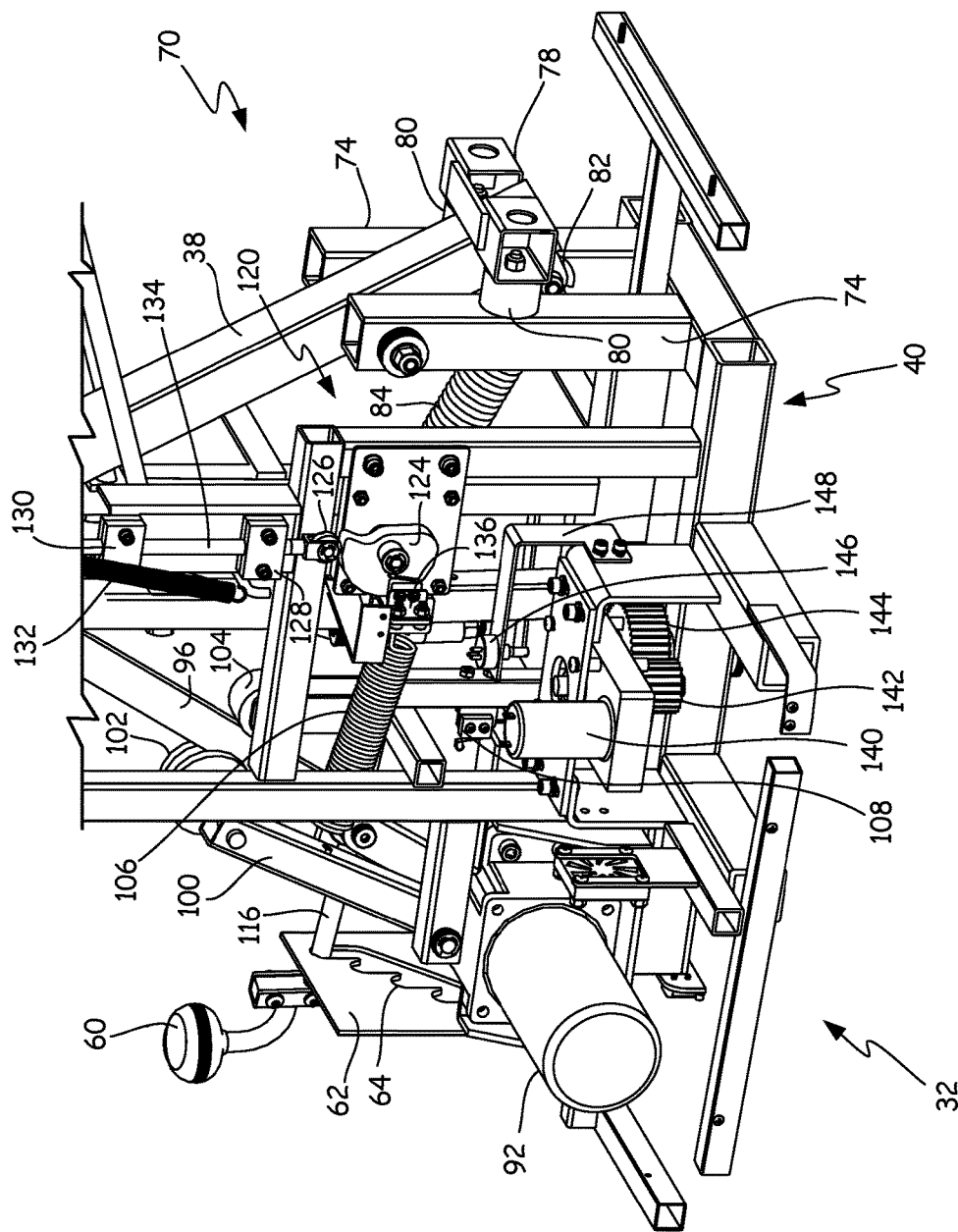
FIG. 8 is a partial perspective view showing the rotation drive of the ball delivery system.

FIG. 8 shows a view of ball launch mechanism 70 of ball launching machine 32 in which the mechanism for rotating ball launch machine 32 with respect to base 20 can be seen. In addition, many of the components of ball launch mechanism 70 that have previously discussed are also labeled and can be seen in FIG. 8. Among those components that have already been discussed are launch arm 38, bottom platform 40 (which is pivotably mounted to base 20 of ball collection system 12), ball distance adjustment knob 60, ball distance pre-select plate 62, and diagonal notched track 64, arm support uprights 74, cross bar 78, bumpers 80, bracket 82, throw spring 84, drive motor 92, grab arm 96, guide arm 100, movable guide wheel 102, stationary guide wheel 104, guide arm spring 106, and drive motor sensor 108. Components of toggle arm actuator mechanism 120 seen in FIG. 8 include cam 124, cam follower guide wheel 126, guide blocks 128 and 130, spring 132, toggle rod 134, and ball feeder sensor 136.

The rotation drive mechanism shown in FIG. 8 includes rotation gear motor 140, rotatable spur gear 142, stationary spur gear 144, rotation potentiometer 146, and potentiometer bracket 148. Platform 40 is rotated with respect to base 20 by rotation of rotatable spur gear 142 with respect to stationary spur gear 144. Spur gear 142 is driven by rotation gear motor 140. Stationary spur gear 144 is mounted on a shaft that is connected to base 20 (shown in FIG. 1). As rotatable spur gear 142 rotates, base 40 and all of the components mounted to base 40 rotate about the axis of the shaft on which stationary spur gear 144 is mounted. Rotation gear motor 140 can drive rotatable spur gear 142 in either a clockwise or a counterclockwise direction. Potentiometer 146 is connected to the shaft on which stationary spur gear 144 is mounted, and produces a variable resistance that is a function of the rotational position of platform 40.

Figure 9:
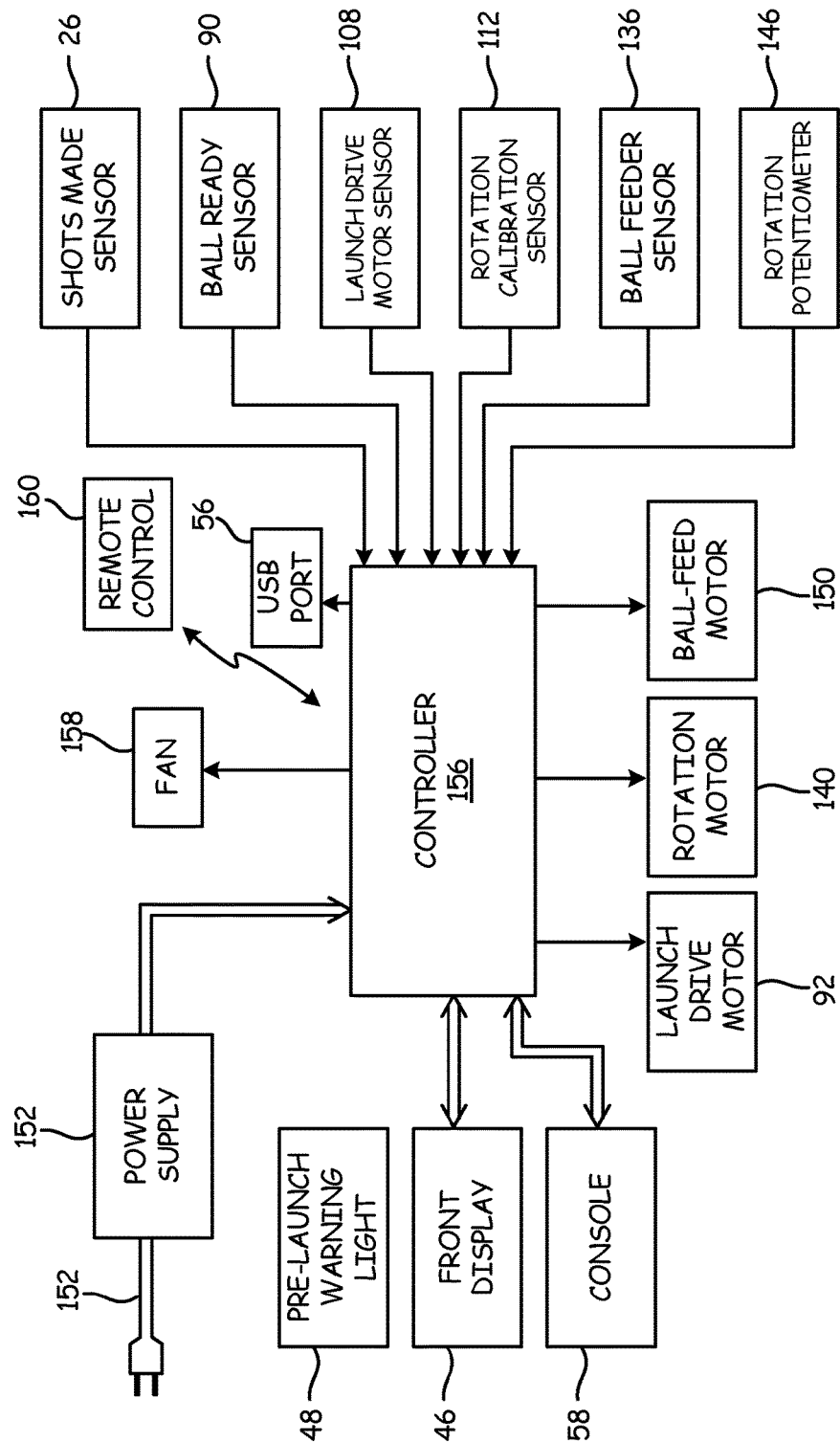
FIG. 9 is a block diagram of the control system of the ball delivery system.

FIG. 9 is a block diagram of the control system of ball delivery system 14. Shown in FIG. 9 shot made sensor 26, are front display 46, pre-launch warning light 48, USB port 56, console 58, ball ready sensor 90, launch drive motor sensor 108, rotation calibration sensor 112, ball feeder sensor 136, rotation motor 140, rotation potentiometer 146, ball feeder toggle motor 150, power supply 152, AC cable 154, controller 156, fan 158, and remote control 160.

Controller 156 is a microprocessor based controller that coordinates the operation of display board 46, safety light 48, console 58, motors 92, 140, and 150, and fan 158. Controller 156 receives input data and commands from console 58 and remote control 160. It also can supply data that is stored to a storage device (such as a flash drive or a computer) through USB port 56. Sensors 26, 90, 108, 136, and potentiometer 146 are used by controller 156 in coordinating and controlling the operations of motors 92, 140, and 150. Calibration sensors 112 are used by controller 156 during set up to provide calibration of the signal from potentiometer 146, which is used to determine the rotational position of ball launching machine 32.

Figure 10:
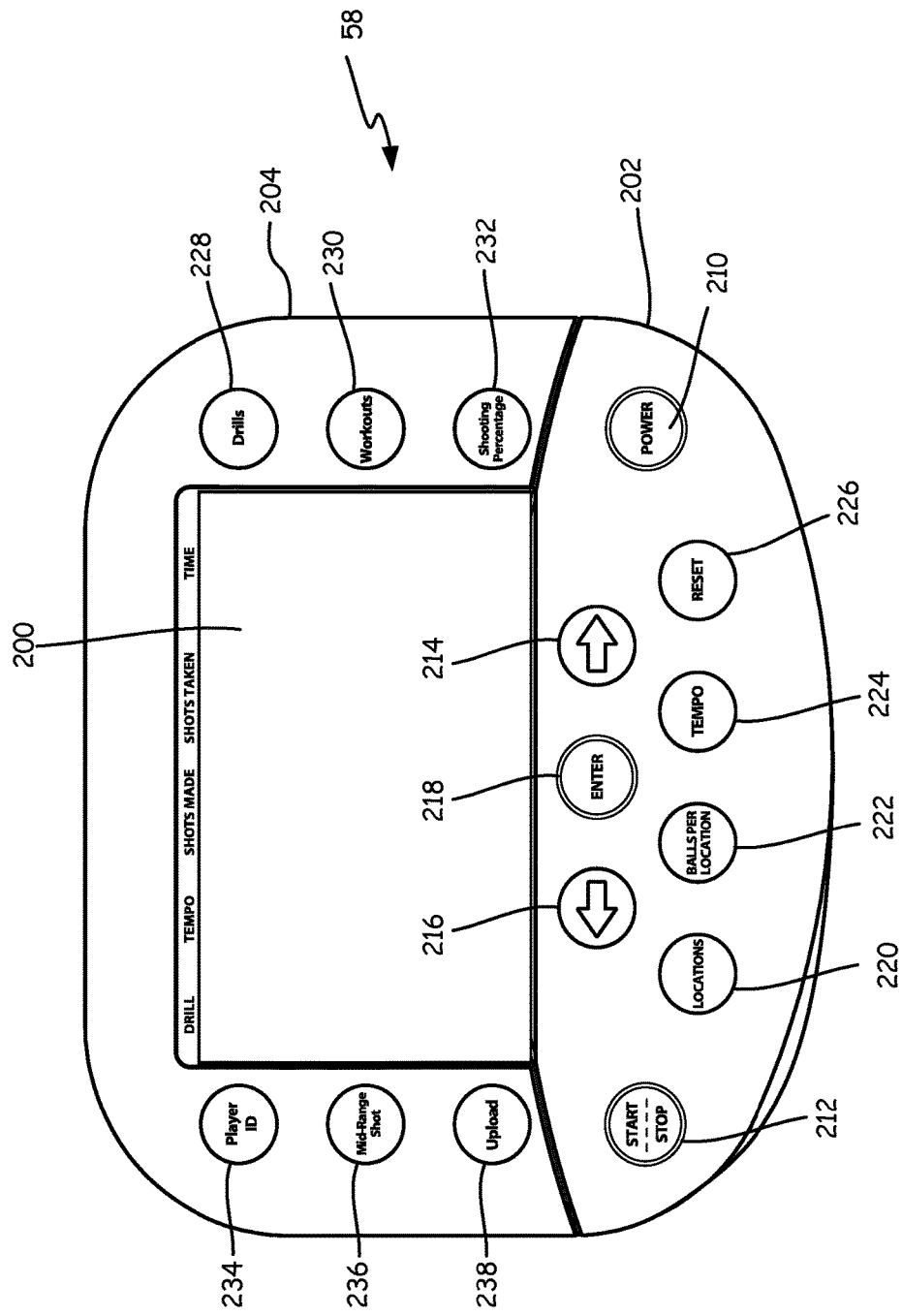
FIG. 10 shows the keyboard and display of the console of the ball delivery system.

FIG. 10 is an illustration of a screen of console 58. In one embodiment, console 58 includes a liquid crystal display (LCD) touchscreen with display area 200 for displaying information and data such as the particular drill performed, the tempo at which the drill was performed, the number of shots made, the number of shots taken, and the elapsed time. Console 58 also includes basic control keyboard area 202 and advanced keyboard area 204. Basic control keyboard 202 includes Power key 210, Start Stop key 212, increase key 214, decrease key 216, Enter key 218, Locations key 220, Balls Per Location key 222, Tempo key 224, and Reset key 226. One other basic control key, Drills key 228 is located within advanced controls keyboard area 204.

The advanced control keys found in advance controls keyboard area 204 include Workouts key 230, Shooting Percentage key 232, Player ID key 234, Mid-Range Shot key 236, and Upload key 238.

The functions of the basic controls are as follows: Power key 202 powers on ball delivery system 14. Start/Stop key 212 starts and stops a workout or drill. Keys 214 and 216 increase and decrease a setting, respectively. Enter key 218 accepts settings. Locations key 220 allows the user to select or edit throwing locations. Balls Per Location key 222 allows the user to edit the number of balls that will be passed to each selected location. Tempo key 224 allows the user to edit the time elapsed between each ball being passed. Reset key 226 resets the current settings. Drills key 228 selects a pre-programmed drill or workout.

The functions of the advanced controls are as follows: Workouts key 230 selects a workout program. Shooting Percentage key 232 allows user to view shooting percentage by location after a workout. Player ID key 234 allows the user to enter a player's initials or code. This is used for shooting statistics uploading. Mid-Range Shot key 236 selects a mid-range jump shot versus a 3 point shot. This is also used when uploading shooting statistics. Upload key 238 allows data from a workout to be uploaded through USB port 56 to a storage device, such as a flash drive or a computer.

In one basic workout, the user simply wishes to shoot from a single location. The user aims ball launching machine 32 in the direction that the user wants to pass the ball. The aiming of ball launching machine 32 is achieved by pressing Enter key 218 while pressing the appropriate increase or decrease key 214 or 216. When ball launching machine 32 is aimed at the desired location, the user presses Start/Stop key 212. To adjust the tempo during this workout, the user presses Tempo key 224.

A workout can also involve shooting from multiple locations. In that case, the user presses Locations key 220. A display then appears on screen 200 showing an arc with a series of numbered locations. A flashing location indicates the current position of a cursor. The user makes use of keys 214 and 216 to move the cursor from one position to another. To select a particular location, the cursor is moved to that location, and the user presses Enter key 218. To deselect a location, the user also presses Enter key 218.

User presses Balls Per Location key 222 to choose the number of balls to be passed to the selected locations. Tempo key 224 is pressed to choose the desired time between each ball passed. Once the workout has been defined in terms of locations, balls per location, and tempo, the user presses Start/Stop key 212. The workout can be paused and resumed by using Start/Stop key 212 or remote control 160.

Controller 156 can store pre-programmed drills. The pre-programmed drills may be preloaded into controller 156 so they are available when basketball training machine 10 is delivered to a customer, or may be developed and loaded into the machine at a later time.

To choose a pre-programmed drill, the user presses Drills key 228. Each pre-programmed drill will be called up in sequence as the user continues to press Drills key 228. When the desired drill is reached, the user presses Start/Stop key 212. The user can then edit any drill by simply changing the setting using Locations key 220, Balls Per Location key 222, Tempo key 224, or Workouts key 230.

To save a new drill, the user presses Drills key 228 and then chooses the drill number that he or she wishes to save. The user then makes use of Locations key 220, Balls Per Location key 222, Tempo key 224, and optionally Workouts key 230 to choose drill settings. Once the drill settings are chosen, the user presses Drills key 228 again. Enter key 218 is then pressed and held until screen 200 displays "Drill Saved".

Remote control 160 communicates wirelessly with controller 156. Remote control 160 can be used to pause and resume any workout. It can also be used in remote mode to pass a ball. A remote mode is activated at console 58 by pressing Tempo key 224 and then using keys 214 and 216 to select the remote mode. The user then presses Start/Stop key 212. The user can then press one of the buttons on remote control 160 to pause ball launching machine 32 to pass a ball. To exit the remote mode, the user changes tempo using Tempo key 224 and keys 214 and 216, or presses Reset key 226.

A user can select a workout program before or after entering settings with Locations key 220, Balls Per Location key 222, and Tempo key 224. When selecting a workout program, the user presses Workouts key 230. There are several types of workouts that can be selected by the user.

A time workout allows the user to set the amount of time the user wants to train. Controller 156 will stop ball launching machine 32 once the selected time has expired.

A shots taken workout allows the user to set out a total of shots to be taken. Controller 156 will automatically stop once the total number of shots goal has been met. This is determined by counting the number of ball launching cycles have occurred since the start of the workout.

A shots made workout allows the user to set an amount of total shots that have to be made during the workout. Controller 156 will count shots made using inputs from shots made sensor 26, and will automatically stop machine 32 when the shots made goal has been met.

A compete workout allows the user to set the amount of shots made required before controller 156 will cause machine 32 to throw to the next location. This can be used in conjunction with other workouts. The number of shots made is determined by controller 156 based upon inputs from shots made sensor 26. For the compete mode, more than one location must have been selected as part of the workout.

A two player compete mode allows selection of a location for each player. Front display 46 shows the amount of shots made by each player. After the workout, the users can press Shooting Percentage key 232 to view individual stats.

The user can view real-time shooting statistics with ball launching machine 32. Statistics can be viewed after a workout has elapsed or by pressing start stop key 212 to pause a current workout. If shots made sensor 26 is connected (i.e., is being used), the average shooting percentage is calculated by controller 156 and displayed on screen 200. The shooting percentages obtained by pressing Shooting Percentage key 232. Shots made, shots taken, time, and shooting percentage show statistics per location. The user can arrow through each selected location using keys 214 and 216 to view the individual statistics for each position on the court.

Tracking a 2-point versus 3-point shot can also be provided. Before pressing Start/Stop key 212 on any workout, the user first presses Mid-Range Shot key 236. As a result of that key press, controller 156 now assumes all shots taken are from inside the 3-point line. To exit mid-range mode, the user again presses Mid-Range Shot key 236. To track free throw shooting, the user presses Locations key 220 and uses keys 214 and 216 to go to the center most location. The user then presses and holds Enter key 218 for two seconds. To exit free throw shooting tracking, the user deselects the center location by pressing Enter key 218 or pressing Reset key 226.

Statistics can be uploaded to a flash drive that is attached to USB port 56. To upload shooting statistics, a player ID must first be entered prior to starting a workout. A date and time must be entered using settings mode. Settings mode can be entered by powering on machine 32 or by pressing Reset key 226. Keys 214 and 216 are then pressed simultaneously and held for two seconds. Then keys 214 and 216 can be used to move between various selections such as selecting time and date. Enter key 218 is used to navigate in the settings mode.

To enter a player ID into controller 156, Player ID key 234 is pressed. A user's three character ID is then entered. Once the player ID has been entered, the user can choose a drill, or set up a workout and press Start/Stop key 212.

When the workout has ended, a USB flash drive is inserted into USB port 56. The user then presses Upload key 238. This causes the shooting statistics to be saved by controller 156 to USB flash drive in USB port 56. The statistics are saved as a single file. This process can be repeated many times as long as there is sufficient space on the flash drive.

Statistics can also be uploaded to the internet after an account has been setup at a designated website, such as www.airborneathletics.com. The USB flash drive that was used to receive uploaded statistics from controller 156 can be connected to a computer which is then logged into the website. Statistics can then be uploaded through the internet to that website.

Coaches can create an account at the website, create a group, and send an email invite to all the players that will be using basketball training machine 10. Each player can click the link at the website and create his or her own profile. By joining the group, the coach can see all of the player's statistics that have been uploaded by each player from controller 156 to a USB flash drive, and from the flash drive to a computer, and then to the website.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A ball launching machine comprising:
 a ball ready holder for receiving a ball to be launched;
 a pivotally mounted launch arm having an upper end and a lower end;
 a throw spring connected to the launch arm;
 a grab arm configured to grab, pull, and release the upper end of the launch arm; and
 a launch drive mechanism for driving the grab arm through a launch drive cycle in which the grab arm pulls the upper end of the launch arm away from the ball to be launched in a rearward and downward arc while increasing spring force of the throw spring, and then releases the upper end of the launch arm so that the throw spring drives the upper end of the launch arm in an upward and forward arc to strike the ball and launch the ball off the ball ready holder, wherein the launch drive mechanism further comprises a guide for engaging the grab arm to guide the grab arm through the launch drive cycle.

2. The ball launching machine of claim 1, wherein the launch arm is pivotally mounted to pivot about a pivot axis located between the upper end and the lower end.

3. The ball launching machine of claim 2, wherein the throw spring is connected to the lower end of the launch arm.

4. The ball launching machine of claim 3, wherein the grab arm has an upper end and a lower end, wherein the upper end of the grab arm includes a hook, and wherein the lower end of the grab arm is connected to the launch drive mechanism.

5. The ball launching machine of claim 4, wherein the launch drive mechanism comprises:
 a drive motor;
 a crank arm connected between a drive shaft of the drive motor and the lower end of the grab arm.

6. The ball launching machine of claim 4, wherein the launch arm includes a grab pin at the upper end of the launch arm that is grabbed, pulled, and released by the hook of the grab arm.

7. The ball launching machine of claim 3 and further comprising:
 an adjustable throw spring tensioner connected to the throw spring.

8. The ball launch machine of claim 1 and further comprising:
 a ball feeder for holding balls to be delivered to the ball ready holder.

9. The ball launch machine of claim 8 and further comprising:
 a toggle arm for delivering a ball one at a time from the ball feeder to the ball ready holder.

10. The ball launch machine of claim 9, wherein the ball ready holder has a forward upper end and a rearward lower end, and wherein the toggle arm delivers the ball from the ball feeder to the upper end of the ball ready holder.

11. The ball launch machine of claim 10, wherein a ball ready sensor is positioned at a launch position at the lower end of the ball ready holder, and wherein the launch drive mechanism initiates the launch drive cycle in response to a ball ready signal from the ball ready sensor.

12. A basketball training machine comprising:
 a ball collection system for collecting basketballs from made and missed shots; and
 a ball delivery system for receiving basketballs from the ball collection system and launching basketballs to selected locations to allow a player or players to shoot the basketballs, the ball delivery system comprising:
  a ball feeder for receiving basketballs from the ball collection system; and
  a rotatable ball launching machine comprising:
   a ball ready holder positioned to receive a single basketball from the ball feeder and position the basketball at a launch position; and
   a ball launch mechanism mounted on a rotatable base and having a spring loaded pivotable launch arm that strikes the basketball to launch the basketball off of the ball ready holder, wherein an upper end of the launch arm is pulled away from the launch position in a downward and rearward arc while spring force on the pivot arm is increased, and the upper end of the launch arm is then released so that the spring force drives the upper end of the launch arm in an upward and forward arc to strike the basketball and launch the basketball off from the ball ready holder, wherein the ball launch mechanism includes:
    a throw spring connected to the launch arm;
    a grab arm configured to grab, pull, and release the launch arm;
    a launch drive mechanism for driving the grab arm through a launch drive cycle; and
    a guide that engages the grab arm and guides movement of the grab arm through the launch drive cycle.

13. The basketball training machine of claim 12, wherein the launch arm includes a lower end, and wherein the launch arm is pivotally mounted to pivot about a pivot axis located between the upper end and the lower end, and wherein the throw spring is connected to the lower end of the launch arm.

14. The basketball training machine of claim 13, wherein the grab arm has an upper end and a lower end, wherein the upper end of the grab arm includes a hook, and wherein the lower end of the grab arm is connected to the launch drive mechanism.

15. The basketball training machine of claim 13, wherein the launch drive mechanism comprises:
   a drive motor;
   a crank arm connected between a drive shaft of the drive motor and the lower end of the grab arm.

16. The basketball training machine of claim 14, wherein the launch arm includes a grab pin at the upper end of the launch arm that is grabbed, pulled, and released by the hook of the grab arm.

17. The basketball training machine of claim 16, wherein the ball launch mechanism further includes:
   an adjustable throw spring tensioner connected to the throw spring.

18. The basketball training machine of claim 12, wherein the ball delivery system further comprises:
   a toggle arm for delivering a ball one at a time from the ball feeder to the ball ready holder;
   wherein a ball ready sensor is positioned at a launch position at the lower end of the ball ready holder, and wherein the launch drive mechanism initiates the launch drive cycle in response to a ball ready signal from the ball ready sensor.

\* \* \* \* \*